United States Patent
Yang et al.

(10) Patent No.: US 12,404,534 B1
(45) Date of Patent: Sep. 2, 2025

(54) METHOD FOR SEPARATING AMOXICILLIN AND PHENYLACETIC ACID FROM REACTION SOLUTION IN ONE-STEP ENZYMATIC SYNTHESIS OF AMOXICILLIN

(71) Applicant: XINGZHI COLLEGE ZHEJIANG NORMAL UNIVERSITY, Lanxi (CN)

(72) Inventors: Zhonghua Yang, Lanxi (CN); Xiaoyan Yin, Lanxi (CN)

(73) Assignee: XINGZHI COLLEGE ZHEJIANG NORMAL UNIVERSITY, Lanxi (CN)

( * ) Notice: Subject to any disclaimer, the term of this patent is extended or adjusted under 35 U.S.C. 154(b) by 0 days.

(21) Appl. No.: 19/223,085

(22) Filed: May 30, 2025

(30) Foreign Application Priority Data

Oct. 29, 2024 (CN) .......................... 202411522210.7

(51) Int. Cl.
| | |
|---|---|
| C12P 37/00 | (2006.01) |
| C07C 51/43 | (2006.01) |
| C07D 499/68 | (2006.01) |
| C12N 9/84 | (2006.01) |
| C12N 11/00 | (2006.01) |

(52) U.S. Cl.
CPC .............. *C12P 37/00* (2013.01); *C07C 51/43* (2013.01); *C07D 499/68* (2013.01); *C12N 9/84* (2013.01); *C12N 11/00* (2013.01); *C12Y 305/01011* (2013.01)

(58) Field of Classification Search
CPC .... C12N 9/84; C12Y 305/01011; C12P 37/00
See application file for complete search history.

(56) References Cited

U.S. PATENT DOCUMENTS

| | | | |
|---|---|---|---|
| 6,403,356 B1 | 6/2002 | You et al. | |
| 2010/0143968 A1* | 6/2010 | Behrouzian | C12P 37/06 435/254.2 |

FOREIGN PATENT DOCUMENTS

| | | |
|---|---|---|
| CN | 1158638 A | 9/1997 |
| CN | 102660621 A | 9/2012 |
| CN | 105274082 A | 1/2016 |
| CN | 107937472 A | 4/2018 |
| WO | 2022195603 A1 | 9/2022 |

OTHER PUBLICATIONS

Andria L.Deaguero, et al., Improving the diastereoselectivity of penicillin G acylase for ampicillin synthesis from racemic substrates, Protein Engineering, Design & Selection, 2012, pp. 135-144, vol. 25, No. 3.
M.R. Green, et al., Molecular Cloning: A Laboratory Manual (Fourth Edition) (Chinese Edition, translated by H. Fuchu), Beijing: Science Press, 2013, pp. 73-76+126-130+364-373, vol. 1.

* cited by examiner

*Primary Examiner* — Thane Underdahl
(74) *Attorney, Agent, or Firm* — Bayramoglu Law Offices LLC

(57) ABSTRACT

A method for separating amoxicillin and phenylacetic acid from reaction solution in one-step enzymatic synthesis of amoxicillin is provided. The method employs immobilized penicillin acylase mutant to catalyze the one-step synthesis of amoxicillin from penicillin potassium, and develops a separation process for the resulting reaction mixture. The technical scheme mainly comprises: Firstly separating the immobilized penicillin acylase mutant from the reaction solution through filtration; subsequently isolating amoxicillin via crystallization; followed by separating and recovering phenylacetic acid through toluene extraction and back extraction. This separation method enables rapid and efficient isolation of amoxicillin with high production yield, achieving an average crystallization rate of 93.22%. Concurrently, it demonstrates effective separation and recovery of phenylacetic acid while allowing recyclable use of the toluene extractant.

7 Claims, 7 Drawing Sheets

Specification includes a Sequence Listing.

```
  1    MKNRN PMIVN GIVTS LICCS SLSAL AASPP TEVKI VRDEY GMPHI YADDT
 51    YRLFY GYGYV VAQDR LFQME MARRS TQGTV SEVLG KAFVS FDKDI RQNYW
101    PDSIR AQIAS LSAED KSILQ GYADG MNAWI DKVNA SPDKL LPQQF STFGF
151    KPKHW EPFDV AMIFV GTMAN RFSDS TSEID NLALL TALKD KYGKQ QGMAV
201    FNQLK WLVNP SAPTT IAARE SAYFL KFDLQ NTQTA ALLFK YDDPA FMLDR
251    FANGT PGALL ALTAD QNRET IAAQF AQSGA NGLAQ YPTTS NKKVI GENKA
301    QQAKA IMVNG PQFGW YAPAY TYGIG LRGAG YDVTQ NTFFA YPGLV FGHNG
351    TISNG STAGF GDPVD IFARK LSAEK PGYYQ HNGEW VSMLS RKETI AVKDG
401    QEEFF TVNKT LHGNV IKTDT AUQTA YASAK AWDSK EVASL LAWTH QMKAK
451    HNPEW TQQAA KQALT INWYY ADVNG NIGYV HTGAY PDRQE GHDPR LPVFG
501    TGSND WKGLL SFDLN PKVYN PQSGY IANKN NSPQK DYPAS DLFAK LWGGA
551    DKVTR IDTIL DKQPR FTADQ AWDVI PQTSR PDLNL RLFLF ALKDA TANLA
601    ENLER RQLVD KLASW DGENL VNDDG KTYQQ PGSAI LNAWL TSMLK RTVVA
651    AVPAP FGKWY SASGY KTTQD GPTGS LNISV QAKIL YEALQ GDKSP IPQAY
701    DLFGG KPQDE VLLAA LDDAN QTLSK KYGND VTGWK TPAMA LTFKA NNFPG
751    VFQAA AKEAK HQAEY QNRGT SNDMI VFSPT SGNPP VLAND VVAPG QGGFI
801    APLGK ADKHY DDQLI MYESF GRRSL WLTFQ PVDEH KESQE VIQVQ R
```

FIG. 2

METHOD FOR SEPARATING AMOXICILLIN AND PHENYLACETIC ACID FROM REACTION SOLUTION IN ONE-STEP ENZYMATIC SYNTHESIS OF AMOXICILLIN

CROSS REFERENCE TO THE RELATED APPLICATIONS

This application is based upon and claims priority to Chinese Patent Application No. 202411522210.7, filed on Oct. 29, 2024, the entire of which are incorporated herein by reference.

SEQUENCE LISTING

The instant application contains a Sequence Listing which has been submitted in XML format via EFS-Web and is hereby incorporated by reference in its entirety. Said XML copy is named FSJZ0102S_Sequence_Listing, created on 05/08/2025, and is 18,431 bytes in size.

TECHNICAL FIELD

The present invention pertains to the technical field of product separation in the enzymatic synthesis of antibiotics, and more specifically relates to a method for separating amoxicillin and phenylacetic acid from a reaction solution produced by a one-step enzymatic catalytic process for preparing amoxicillin.

BACKGROUND

Amoxicillin (AMOX), also known as hydroxyampicillin, serves as a primary member of the second-generation penicillins. As a broad-spectrum semi-synthetic antibiotic, amoxicillin inhibits bacterial cell wall synthesis. Recognized by the World Health Organization (WHO) as the preferred β-lactam oral antibiotic due to its high efficacy, broad antimicrobial spectrum, and minimal adverse effects.

Methods for amoxicillin preparation include chemical synthesis and enzymatic catalysis. Chemical synthesis suffers from prolonged reaction steps, high levels of three wastes (waste gas, wastewater, and solid residues), and excessive use of chemical solvents. With the advancement of green synthesis concepts in pharmaceutical manufacturing and improvements in enzymatic synthesis technology, enzymatic catalytic synthesis has become the predominant method for amoxicillin production. The primary process involves: synthesizing amoxicillin through penicillin acylase-catalyzed reaction of 6-APA with D-p-hydroxy-phenylglycine (or its methyl ester)(e.g., Chinese Patent Application No. 201711221286.6), followed by separation, purification, crystallization, and drying to obtain the final product.

However, challenges persist in enzymatic amoxicillin synthesis. For instance, Chinese Patent CN102660621A discloses a process using 6-APA and D-p-hydroxy-phenylglycine methyl ester, but exhibits low final product yield and poor flowability. Penicillin acylase mutants enable one-step amoxicillin synthesis directly from penicillin and its salts. This technology eliminates multi-step reactions and intermediate product (e.g., 6-APA) separation processes required in conventional methods, offering simplified production, enhanced efficiency, and significantly reduced costs. A critical issue arises in the one-step synthesis reaction solution, which contains equimolar amounts of amoxicillin (AMOX) and phenylacetic acid (PAA). It is necessitating that high-yield isolation of amoxicillin meeting active pharmaceutical ingredient standards and efficient recovery and reuse of phenylacetic acid. Existing separation techniques for multi-step processes cannot meet the purification requirements for one-step synthesis.

SUMMARY

To address the limitations of existing technologies, the present invention provides a production technology for efficiently and rapidly purifying amoxicillin and recovering phenylacetic acid, thereby achieving rapid separation and purification of amoxicillin and large-scale recovery of phenylacetic acid. The amoxicillin produced meets the requirements of pharmaceutical production and complies with active pharmaceutical ingredient standards.

The present invention is implemented as follows: a method for separating amoxicillin and phenylacetic acid from a reaction solution obtained by preparing amoxicillin via one-step enzymatic catalysis. The method is characterized in comprising the steps of:
(1) adding deionized water to the reaction suspension, and performing vacuum filtration to obtain an amoxicillin filtrate and a retained immobilized penicillin acylase mutant;
(2) washing the retained immobilized penicillin acylase mutant with deionized water, and combining the wash solution with the amoxicillin filtrate from step (1);
(3) adjusting the pH of the mixed solution obtained in step (2) to 2 with hydrochloric acid to obtain a separation-ready mixture;
(4) adding a NaOH solution dropwise to the separation-ready mixture until reaching a pH between 3.5 and 5.5, followed by static crystallization at 4° C.; and
(5) after crystallization is complete, filtering to obtain amoxicillin crystals and a liquid phase containing phenylacetic acid.

Preferably, further comprising the following steps after step (5):
(6) adjusting the pH of the liquid phase containing phenylacetic acid to between 2.0 and 2.5, and extracting with toluene to obtain an organic phase containing phenylacetic acid;
(7) subjecting the organic phase containing phenylacetic acid to back-extraction with a NaOH solution, converting phenylacetic acid into sodium phenylacetate in an aqueous phase;
(8) separating the aqueous phase from the organic phase, wherein the toluene organic phase is recycled for extraction in step (6);
(9) adding hydrochloric acid to the aqueous phase containing sodium phenylacetate to adjust the pH to between 2.0 and 2.5, converting sodium phenylacetate into phenylacetic acid, followed by crystallization at 4° C.; and
(10) after crystallization is complete, filtering to separate and recover phenylacetic acid crystals.

Preferably, in step (3), the hydrochloric acid concentration is 15% by volume.

Preferably, in step (4), the pH for amoxicillin crystallization is 5, and the crystallization time is 9 hours.

Preferably, in step (5), after filtration and separation, the amoxicillin crystals are dried in a vacuum oven at 50° C. for 2 hours.

Preferably, in step (6), the pH is adjusted using 15% by volume hydrochloric acid; extraction with toluene is performed at least twice, and the resulting organic phases are combined.

The method for catalyzing the one-step synthesis of amoxicillin from penicillin potassium using the immobilized penicillin acylase mutant comprises: using only one penicillin acylase mutant as a sole enzyme in a reaction system, using the penicillin or the salt thereof and D-p-hydroxyphenylglycine methyl ester as substrates, and carrying out a reaction in a buffer system of pH 4-8; wherein compared with the amino acid sequence shown in SEQ ID NO: 1, an amino acid sequence of the penicillin acylase mutant comprises at least one of the following mutations: F146αK, F24βR, F71βY, N241βK, G385βY, or G385βR.

Process specifically includes the following steps:
S1: adding a buffer solution of pH 4-8 to a reaction flask as a reaction buffer system;
S2: adding a penicillin potassium salt and the D-p-hydroxyphenylglycine methyl ester to the reaction buffer system, wherein a molar ratio of the penicillin potassium salt to the D-p-hydroxyphenylglycine methyl ester is 1:1-1:2, and stirring thoroughly; and
S3: adding an immobilized penicillin acylase mutant to the reaction buffer system, and reacting at a reaction temperature controlled at 12-30 C°. The preferred reaction temperature is 12 to 28° C.

Preferably, wherein the buffer solution in the step S1 comprises any one of citric acid buffer, acetic acid buffer, phosphate buffered saline (PBS) buffer, sodium dihydrogen phosphate-citric acid buffer, sodium barbital-hydrochloric acid buffer, and pure water.

Preferably, wherein in the step S2, a concentration of the penicillin potassium salt is 50-200 mmol/L, and a concentration of D-p-hydroxyphenylglycine methyl ester is 50-400 mmol/L.

Preferably, wherein in the step S3, an amount of the immobilized penicillin acylase is 3000-30000 U/L, and a reaction time is 1-6 h.

In summary, the advantages and positive effects of the present invention are as follows: the present invention uses an immobilized penicillin acylase mutant to catalyze the one-step synthesis of amoxicillin from potassium penicillin. A set of methods for separating amoxicillin and phenylacetic acid from the resulting reaction mixture has been developed. The technical scheme mainly includes the following: first, the immobilized penicillin acylase is separated from the reaction mixture by filtration; then, amoxicillin is isolated through crystallization; thereafter, phenylacetic acid is recovered through toluene extraction, back-extraction, and subsequent crystallization. This separation method enables rapid and efficient isolation of amoxicillin with a high yield-achieving an average crystallization rate of 93.22%. At the same time, the separation and recovery of phenylacetic acid is highly effective, and the extraction agent, toluene, can be reused.

BRIEF DESCRIPTION OF THE DRAWINGS

FIG. 2 shows the amino acid sequence (SEQ ID NO: 1) of the wild-type penicillin acylase enzyme.

DETAILED DESCRIPTION OF THE EMBODIMENTS

For clarity and to avoid limiting the scope of the invention, all numerical values expressing quantities, percentages, or other parameters in this application shall be interpreted as being modified by the term "about." Unless explicitly stated otherwise, all numerical parameters in the specification and claims are approximations that may vary depending on the desired properties sought to be achieved. These numerical parameters should be interpreted in light of the reported significant digits and conventional rounding techniques. As used herein, "about" means within ±10% of a stated value or range, preferably within ±5%.

Ambient temperature: Unless otherwise specified, experiments are conducted under ambient conditions (natural room temperature without additional cooling/heating), typically defined as 10 to 30° C., preferably 15 to 25° C. Abbreviations: "min" (minute), "s" (second), "U" (enzyme activity unit), "mM" (millimolar per liter), "M" (molar per liter), "rpm" (revolutions per minute), "mol" (mole), "μg" (microgram), "mg" (milligram), "g" (gram), "μL" (microliter), "mL" (milliliter), "bp" (base pair), "LB medium" (Luria-Bertani medium), "Kan50" (medium containing 50 μg/mL kanamycin).

For experimental methods not specified with specific conditions in the examples, conventional conditions were typically followed, such as those described in the "Molecular Cloning: A Laboratory Manual" (Chinese Edition) (J. Sambrook, M. R. Green, translated by H. Fuchu, 4th edition, Beijing: Science Press, 2017) and in New England Biolabs (NEB) kits.

Figure 1:
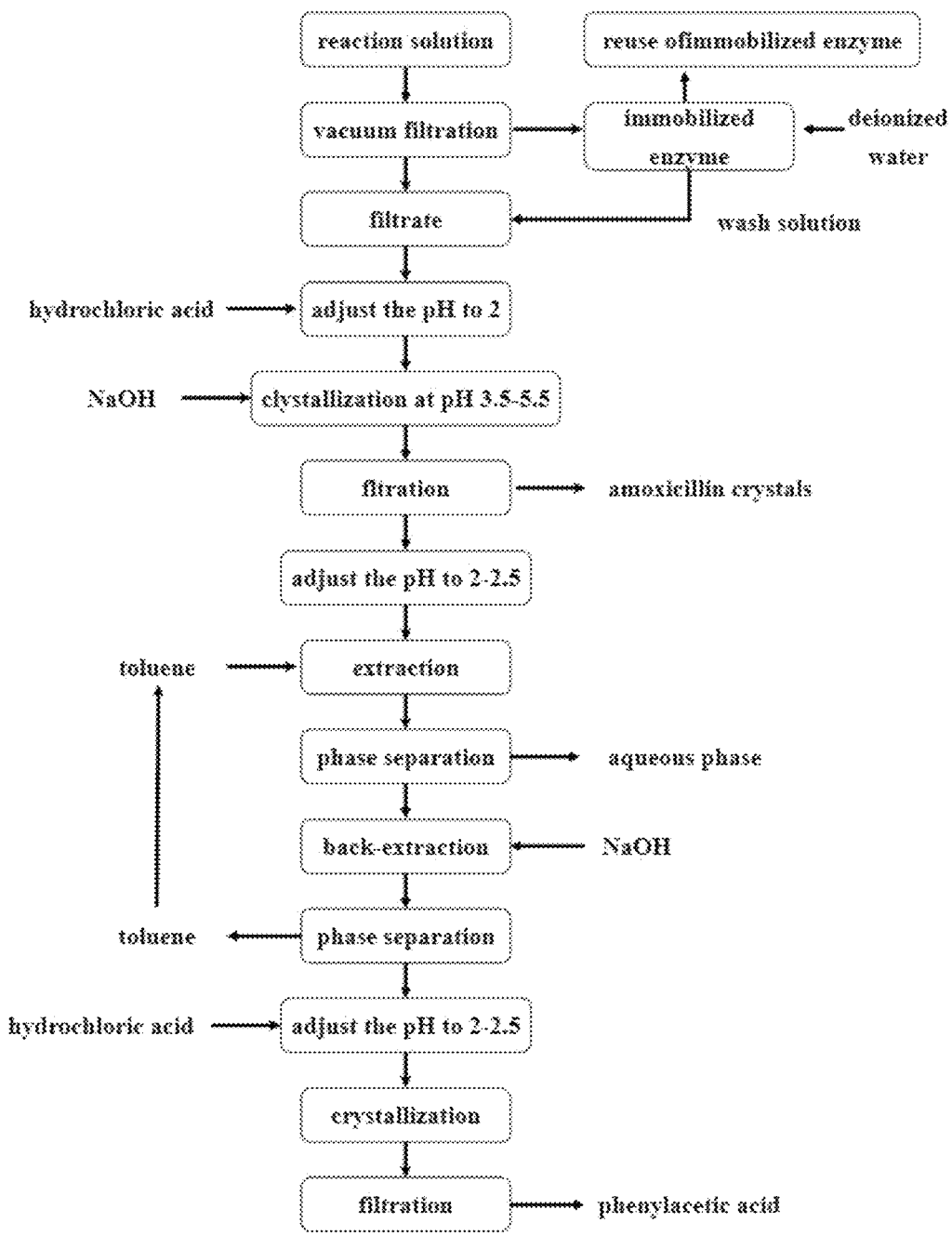
FIG. 1 is a schematic flow diagram illustrating a method for separating amoxicillin and phenylacetic acid from a reaction mixture obtained by one-step enzymatic synthesis of amoxicillin.

The present invention discloses a method for separating amoxicillin and phenylacetic acid from a reaction mixture obtained by one-step enzymatic synthesis of amoxicillin. The main content includes: first, using an immobilized penicillin acylase mutant to catalyze the one-step synthesis of amoxicillin from potassium penicillin, obtaining a reaction suspension, and then performing separation processing on the reaction suspension. The main steps include: (1) Under ambient temperature conditions, adding an equal volume of deionized water to the reaction suspension, filtering under normal pressure to obtain a filtrate containing amoxicillin and a retained immobilized penicillin acylase; (2) Washing the retained immobilized penicillin acylase with deionized water, combining the washing solution with the amoxicillin filtrate obtained in step (1); (3) Adjusting the pH of the mixed solution obtained in step (2) to 2 using hydrochloric acid, filtering to obtain an amoxicillin reaction solution; (4) Adjusting the pH of the amoxicillin reaction solution to 5.0 with a 0.25 M NaOH solution for crystallization, allowing the solution to crystallize at 4° C. for 9 hours. After completion of crystallization, separating solids from liquids to obtain amoxicillin crystals and a liquid phase containing phenylacetic acid; (5) Adjusting the pH of the liquid phase containing phenylacetic acid to between 2.0 and 2.5, extracting with toluene to transfer phenylacetic acid from the aqueous phase into the organic phase; (6) Adding a 0.25 M NaOH solution to the aforementioned organic phase to convert phenylacetic acid into sodium phenylacetate, which enters the aqueous phase; (7) Under heating conditions, adding 15% hydrochloric acid to the aforementioned aqueous phase containing sodium phenylacetate to adjust the pH to 2-2.5, converting sodium phenylacetate back into phenylacetic acid, and allowing it to crystallize at 4° C. The process flowchart is shown in FIG. 1.

The following will describe the technical solutions of the present invention clearly and completely in conjunction with the embodiments of the present invention.

Embodiment 1

Construction of the Prokaryotic Expression for the Mutant of Penicillin Acylase from *Kluyvera citrophila*, and its Functional Characterization 1. Construction of Wild-Type PA Expression Vector pET28a-kcPA The wild-type penicillin acylase used in this Embodiment originates from *Kluyvera citrophila* ATCC 21285. Its amino acid sequence (SEQ ID NO: 1) comprises four domains, the sequence from the N-terminus to the C-terminus of the protein is as follows: Signal peptide: Positions 1-26. α-subunit: Positions 27-235 (209 amino acids). Linker peptide: Positions 236-289 (54 amino acids). β-subunit: Positions 290-846 (557 amino acids). Refer to FIG. 2 for domain annotations (single underline: α-subunit; wavy line: linker; double underline: β-subunit). The nucleotide sequence is provided as SEQ ID NO: 2.

Figure 3:
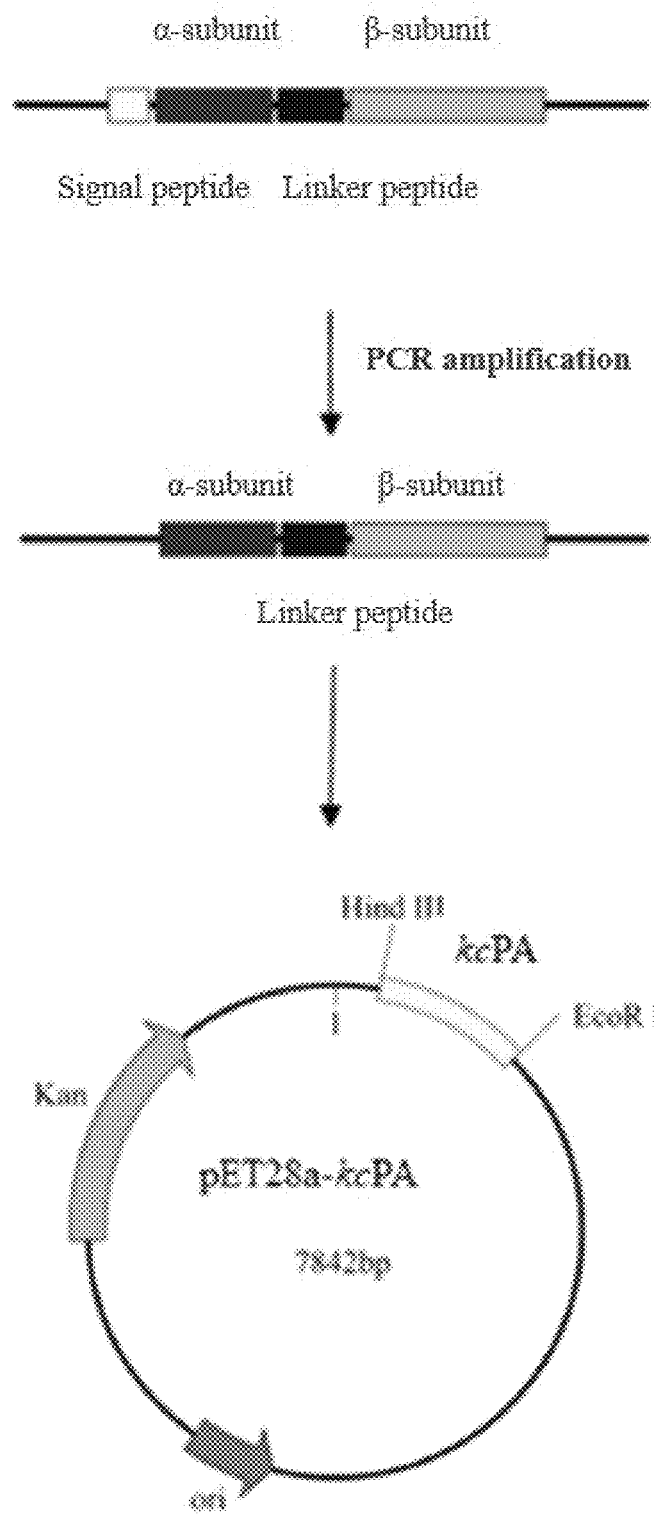
FIG. 3 is a schematic diagram of the construction of the recombinant plasmid pET28a-kcPA.

The recombinant plasmid pET28a-kcPA was constructed as illustrated in FIG. 3. Using genomic DNA from *K. citrophila* ATCC 21285 as a template, primers were designed based on the nucleotide sequence of PA (SEQ ID NO: 2): Forward primer (SEQ ID NO: 3): 5'-CGG/AATT-CATGAAAAACCGCAATCGCAT-3'. Reverse primer (SEQ ID NO: 4): 5'-CCA/AGCTTT-TAGCGCTGCACCTGCAGC-3'. EcoRI and HindIII restriction enzyme sites were introduced into the primer sequences (the underlined bases indicate the restriction enzyme recognition sites), and the target fragment of the wild-type PA was then amplified by PCR.

| PCR Reaction mixture | |
| --- | --- |
| Component | Volume |
| Sterile ddH$_2$O | 10 μL |
| template | 0.5 μL |
| Forward primer (10 μM) | 1 μL |
| Reverse primer (10 μM) | 1 μL |
| 2× Taq Polymerase | 12.5 μL |
| Total reaction volume | 25 μL |

| PCR Thermal Cycling as following: | |
| --- | --- |
| ①. 95° C. | 5 min |
| ②. 95° C. | 45 s |
| ③. 60° C. | 50 s |
| ④. 72° C. | 90 s |
| ⑤. Go to ② | 30 cycles |
| ⑥. 72° C. | 10 min |
| ⑦. 4° C. | forever |

The empty plasmid pET28a and PCR-amplified PA DNA fragment were subjected to double restriction enzyme digestion using EcoRI and HindIII restriction enzymes.

| Double enzyme digestion system: | |
| --- | --- |
| Component | Volume/Amount |
| 10x Buffer | 5 μL |
| EcoRI | 1.5 μL |
| HindIII | 1.5 μL |
| Empty vector or PCR product | 42 μL |
| Total | 50 μL |

The double restriction enzyme digestion was carried out at 37° C. for 1 hour, followed by enzyme inactivation at 80° C. for 20 minutes. The digested products were purified and quantified via agarose gel electrophoresis, yielding approximate concentrations of 50 ng/μL for the pET28a vector and 140 ng/μL for the kcPA insert.

The purified fragments were ligated using T4 DNA ligase in a 16° C. metal bath overnight to generate the recombinant plasmid pET28a-kcPA. The recombinant plasmid was introduced into competent *E. coli* DH5α cells via heat shock transformation.

Connection Reaction System of the Target Fragment and the Linearized Vector:

| Component | Volume |
| --- | --- |
| 10x Buffer | 1 μL |
| T4 DNA ligase | 1 μL |
| Linearized vector | 4 μL |
| Insert fragment | 4 μL |
| Total | 10 μL |

Figure 4:
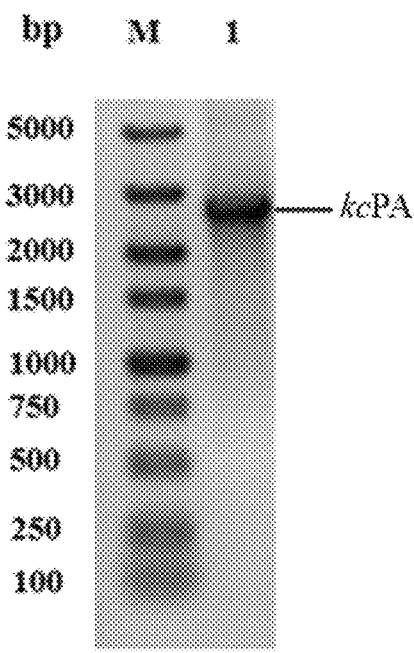
FIG. 4 displays the agarose gel electrophoresis analysis of the PCR-amplified recombinant plasmid.

To verify successful plasmid transformation, single colonies were picked from Kan50-LB agar plates and inoculated into Kan50-LB liquid medium. On the following day, plasmids were extracted using a plasmid extraction kit and subjected to PCR verification. Agarose gel electrophoresis confirmed the presence of a 2500-bp target band (see FIG. 4). The validated expression vector pET28a-kcPA was then transformed into *E. coli* BL21(DE3) to generate the recombinant strain *E. coli* BL21(DE3)/pET28a-kcPA for wild-type PA expression.

2. Generation of Mutant Expression Vectors

In this embodiment, a total of 18 mutants were obtained through site-directed mutagenesis, as shown in the table below. The notation "F146αK" indicates that the amino acid at position 146 on the α subunit was changed from F (Phenylalanine) to K (Lysine). The explanation for other mutation sites follows the same logic.

TABLE 1

Mutants and Corresponding Mutation Sites

| Mutant ID | Mutation Sites |
|---|---|
| KcPA | Wild-type |
| KcPA 01-06 | Single-point mutants: F146αK, F24βR, F71βY, N241βK, G385βY, G385βR |
| KcPA 07-11 | Double-point mutants: F146αK combined with one of F24βR, F71βY, N241βK, G385βY, or G385βR |
| KcPA 12 | Triple-point mutant: F146αK & F24βR & F71βY |
| KcPA 13 | Triple-point mutant: F146αK & N241βK & G385βY |
| KcPA 14 | Triple-point mutant: F146αK & N241βK & G385βR |
| KcPA 15 | Triple-point mutant: F146αK & F71βY & N241βK |
| KcPA 16 | Quadruple-point mutant: F146αK & F71βY & N241βK & G385βY |
| KcPA 17 | Quintuple-point mutant: F146αK & F24βR & F71βY & N241βK & G385βY |
| KcPA 18 | Quintuple-point mutant: F146αK & F24βR & F71βY & N241βK & G385βR |

First, primers corresponding to each mutation site were designed. Then, Using the wild-type PA target fragment as the initial template, site-directed mutagenesis was performed with the NEB Q5® Site-Directed Mutagenesis Kit (Q5 SDM Kit). The primers for each mutation site are listed below (lowercase letters indicate mutated nucleotides):

```
F146αK,
Forward (F): 5'-GGCGAACCGTaaaTCTGACAGCACCAG-3', SEQ ID NO: 5;
Reverse (R): 5'-ATGGTGCCGACAAAAATCATCGCCA-3', SEQ ID NO: 6;

F24βR,
Forward (F): 5'-TGGGCCGCAGcgcGGTTGGTATGCG-3', SEQ ID NO: 7;
Reverse (R): 5'-TTGACCATAATGGCCTTCGCATCCT-3', SEQ ID NO: 8;

F71βY,
Forward (F): 5'-CACCGCCGGTtatGGTGATGATG-3', SEQ ID NO: 9;
Reverse (R): 5'-GATCCCCATGAAATGGTGCCGTTGT-3', SEQ ID NO: 10;

N241βK,
Forward (F): 5'-CGCCAACTGGaaaAACTCGCCGC-3', SEQ ID NO: 11;
Reverse (R): 5'-ATATAGCCCGACTGCGGGTTATACAC-3', SEQ ID NO: 12;

G385βY,
Forward (F): 5'-CGGGCCAACCtatTCGCTGAACATCAGCGTG-3', SEQ ID NO: 13;
Reverse (R): 5'-TCCTGGGTGGTTTCATAGCCACTGG-3', SEQ ID NO: 14;

G385βR,
Forward (F): 5'-CGGGCCAACCcgcTCGCTGAACATC-3', SEQ ID NO: 15;
Reverse (R): 5'-TCCTGGGTGGTTTCATAGCCACTGG-3', SEQ ID NO: 16;
```

The primers were synthesized by a nucleic acid synthesis company, then dissolved in sterile water before proceeding with the protocol according to the kit instructions. As following:

Step 1: Site-Directed Mutagenesis Via PCR

PCR Reaction mixture:

| Component | Volume |
|---|---|
| Q5 Hot Start High-Fidelity 2X Master Mix | 12.5 μL |
| 10 μM Forward Primer | 1.25 μL |
| 10 μM Reverse Primer | 1.25 μL |
| Template DNA (1-25 ng/μL) | 1 μL |
| Nuclease-Free Water | 9.0 μL |
| Total Volume | 25 μL |

Thermal Cycling Program:

| Step | Temperature | Time |
|---|---|---|
| Initial Denaturation | 98° C. | 30 s |
| 25 Cycles | 98° C. | 10 s |
| | 68° C. | 10-30 s |
| | 72° C. | 62 s |
| Final Extension | 72° C. | 2 min |
| Hold | 4-10° C. | ∞ |

For mutants with ≥2 mutation sites, the PCR product from the prior mutation step was used as the template for subsequent rounds of site-directed mutagenesis.

Step 2: Kinase, Ligase & DpnI (KLD) Treatment

Reaction mixture:

| Component | Volume | Final Concentration |
|---|---|---|
| PCR Product | 1 μL | |
| 2x KLD Reaction Buffer | 5 μL | 1x |
| 10x KLD Enzyme Mix | 1 μL | 1x |
| Nuclease-Free Water | 3 μL | |

Incubate at room temperature for 5 minutes.

Step 3: Heat Shock Transformation

Add 5 μL of the KLD reaction mixture to 50 μL of chemically competent E. coli BL21(DE3) cells. Incubate on ice for 30 minutes, apply a 42° C. heat shock for 30 seconds, and return to ice for 5 minutes. Subsequently, add 950 μL of SOC sterile liquid medium and incubate at 37° C. with gentle shaking for 1 hour. Spread 40-100 μL of the bacterial suspension onto Kan50-LB agar plates and incubate overnight at 37° C. The resulting single colonies represent the mutant expression strains, designated as E. coli BL21(DE3)/pET28a-kcPA01~18.

Step 4: Mutant Verification

Inoculate the obtained mutant expression strains into 25 mL of LB liquid medium containing Kan50. Incubate at 37° C. overnight. Use a plasmid extraction kit to isolate the plasmid. Send the plasmid to a third-party biotech company for sequencing to confirm that the product is the intended point-mutated target product.

3. Expression of Wild-Type and Mutant KcPA

The recombinant strains *E. coli* BL21(DE3)/pET28a-kcPA and *E. coli* BL21(DE3)/pET28a-kcPA01~18 were inoculated onto Kan50 LB agar plates and incubated in a 37° C. incubator for 12-16 hours. Single colonies were picked and inoculated into 25 mL of LB liquid medium containing Kan50. These cultures were grown overnight at 37° C. with shaking at 300 rpm. Next, 500 µL of the bacterial suspension was transferred to 50 mL of Kan50 LB liquid medium and incubated at 37° C. with shaking at 280 rpm. The OD600 was monitored, and when it reached 0.6-0.8, IPTG was added to a final concentration of 0.3 mM to induce protein expression. The cultures were induced for 10 hours at 25° C. with shaking at 220 rpm. The cells were harvested by centrifugation, and the cell pellets were resuspended in pre-chilled PBS buffer (pH 7.5) and kept on ice for 10 minutes. The resuspended cells were then centrifuged at 4° C., 12,000 rpm for 6 minutes to collect the cell pellets. The cell pellets were further resuspended in 50 mM PBS buffer (pH 7.5), and after another round of centrifugation at 4° C., 12,000 rpm for 6 minutes, the supernatant was discarded, and the final cell pellets were resuspended at a concentration of 0.01 g/mL. The cells were lysed using a sonicator under the following conditions: ice-water bath, 400 W power, with cycles of 3 seconds on and 5 seconds off for a total of 80 cycles. After lysis, the mixture was centrifuged at 4° C., 12,000 rpm for 15 minutes, and the supernatant was collected as the crude enzyme extract. SDS-PAGE was then used to analyze the expressed proteins.

Figure 5:
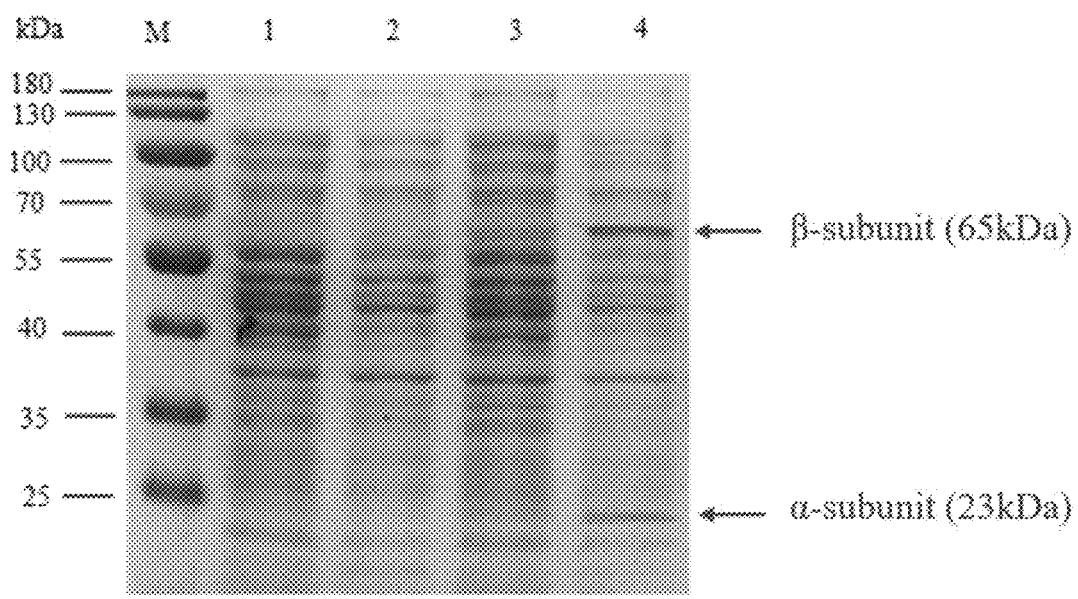
FIG. 5 presents the SDS-PAGE electrophoresis results of protein expression in E. coli BL21(DE3)/pET28a-kcPA cells.

FIG. 5 shows the SDS-PAGE image of expressed proteins. The lanes are labeled as follows: M: Protein marker. Lane 1: Supernatant of *E. coli* BL21(DE3)/pET28a. Lane 2: Supernatant of *E. coli* BL21(DE3)/pET28a-kcPA without induction. Lane 3: Supernatant of *E. coli* BL21(DE3)/pET28a-kcPA18 without induction. Lane 4: Supernatant of IPTG-induced *E. coli* BL21(DE3)/pET28a-kcPA18.

Embodiment 2

1. Measurement of KcPGA Hydrolytic Activity

Principle of Measurement: Penicillin Potassium Salt (PGK) is hydrolyzed under the action of KcPA to produce 6-Aminopenicillanic Acid (6-APA) and phenylacetic acid. Under acidic conditions, 6-APA reacts with p-Dimethylaminobenzaldehyde (PDAB) to form a yellow-green substance that has a maximum absorption peak at 415 nm. The enzyme activity is defined as: in 0.1 M PBS buffer at 28° C., the amount of penicillin acylase required to catalyze the conversion of 20 mg/mL PGK into 1 µmol of 6-APA per minute is defined as KcPA enzyme activity one unit (U).

Weigh 0.5 g of PGK and dissolve it in the aforementioned buffer solution, then adjust the volume to 25 mL. Pipette 2 mL of PGK solution into a centrifuge tube and add 0.1 mL of KcPA enzyme solution. Set up a control without adding KcPA while keeping all other conditions identical.

Place the reaction system in a water bath shaker at 28° C. and 200 rpm for 10 minutes. After the reaction, deactivate the enzyme by placing it in a 90° C. water bath for 2 minutes. Then, take 200 µL of the post-reaction solution and add it to 3 mL of 0.1 M citrate buffer at pH 3.0, followed by the addition of 1 mL of coloring reagent (0.5% PDAB). Allow it to stand at room temperature for 3 minutes before measuring the absorbance at 415 nm. Use the 6-APA standard curve to determine the concentration of 6-APA in the sample, and calculate the enzyme activity, i.e. the hydrolytic activity, using the formula provided.

Calculation Formula: Hydrolytic Activity of Penicillin Acylase Per mL:

$$U = \frac{C_{6-APA} \times V}{t \times V_E}$$

Where, $C_{6-APA}$: Concentration of 6-APA in the sample, µmol/L; V: Volume of the reaction system, mL; $V_E$: Volume of penicillin acylase added, mL; t: Reaction time, 10 min.

2. Measurement of KcPA Synthesis Activity

6-Aminopenicillanic Acid (6-APA) and D-p-Hydroxyphenylglycine methyl ester (D-HPGM) are catalyzed by KcPA to synthesize Amoxicillin. The amount of Amoxicillin can be measured using High-Performance Liquid Chromatography (HPLC), thereby calculating the synthesis activity of Penicillin Acylase (PA). The enzyme activity is defined as: under certain conditions, the amount of enzyme required to catalyze the production of 1 µmol of Amoxicillin per minute is considered one unit of synthesis activity, denoted as U.

Weigh 1 g of 6-APA and 1.25 g of D-HPGM and dissolve them in 50 mL of 0.1 M PBS buffer at pH 6.3. Adjust the pH to 6.3 and then make up to a total volume of 100 mL with the same buffer. Add 0.1 mL of KcPA enzyme solution to this mixture and incubate at 25° C. with shaking at 200 rpm for 30 minutes. Inactivate the enzyme by placing it in a 90° C. water bath for 2 minutes. Filter 0.5 mL of the reaction mixture through a 0.22 µm aqueous filter membrane and dilute with phosphate buffer to 100 mL for HPLC analysis to determine the concentration of Amoxicillin. The formula for calculating enzyme activity is provided below:

Calculation Formula: Synthesis Activity of Penicillin Acylase Per mL:

$$U = \frac{C_{sample} \times V \times 200}{V_E \times t}$$

Where, $C_{sample}$: Concentration of Amoxicillin, µmol/L; V: Volume of the reaction mixture, mL; 200: Dilution factor; $V_E$: Volume of enzyme added, mL; t: Reaction time, min.

HPLC Conditions: Agilent ZORBAX SB-C18 4.6×250 mm column, column temperature 25° C. Injection volume 10 µL. Mobile phase A (0.02 M $NaH_2PO_4$—$Na_2HPO_4$ buffer at pH 4.7), mobile phase B (methanol). Start with 90% mobile phase A and 10% mobile phase B for 5 minutes, increase mobile phase B from 10% to 50% between 5 and 7 minutes, maintain 50% for 10 minutes, reduce mobile phase B from 50% to 10% between 17 and 19 minutes, and finally equilibrate with 90% mobile phase A and 10% mobile phase B for 5 minutes. Total flow rate is 1 mL/min.

TABLE 2

Comparison of Activities Between Mutants and Wild Type

| Mutant ID | Comparison of hydrolysis activity | Comparison of Synthesis Activity |
|---|---|---|
| KcPA | 100 | 100 |
| KcPA 01 | 580 | 1530 |
| KcPA 02 | 245 | 950 |
| KcPA 03 | 286 | 838 |
| KcPA 04 | 290 | 818 |

TABLE 2-continued

Comparison of Activities Between Mutants and Wild Type

| Mutant ID | Comparison of hydrolysis activity | Comparison of Synthesis Activity |
|---|---|---|
| KcPA 05 | 492 | 709 |
| KcPA 06 | 462 | 1118 |
| KcPA 07 | 745 | 2054 |
| KcPA 08 | 786 | 3037 |
| KcPA 09 | 664 | 2260 |
| KcPA 10 | 858 | 3574 |
| KcPA 11 | 920 | 4380 |
| KcPA 12 | 730 | 3410 |
| KcPA 13 | 953 | 8842 |
| KcPA 14 | 1074 | 10568 |
| KcPA 15 | 620 | 4875 |
| KcPA 16 | 831 | 8640 |
| KcPA 17 | 1270 | 12680 |
| KcPA 18 | 1440 | 15620 |

Note: The hydrolytic activity of recombinantly expressed wild-type KcPA is 15 U/mL (fermentation broth), and the synthesis activity is 80 U/mL. For ease of comparison, the enzyme activity of the wild-type KcPA is defined as 100 in Table 2, with each mutant's activity compared against this baseline.

From the table, it is evident that single-site mutants exhibit significantly enhanced hydrolytic and synthesis activities compared to the wild type, particularly F146αK on the α subunit and G385βR on the β subunit. Specifically, the single-point mutation F146αK shows 5.8 times higher hydrolytic activity and 15.3 times higher synthesis activity than the wild type. The G385βR mutant exhibits 4.6 times higher hydrolytic activity and approximately 11.2 times higher synthesis activity than the wild type. Comparing G385βY and G385βR mutants, the former has higher hydrolytic activity but not superior synthesis activity. When multiple mutations are combined, the enzyme activity increases significantly over single mutations, especially for the five-point mutant F146αK & F24βR & F71βY & N241βK & G385βR, which shows high levels of both hydrolytic and synthesis activities.

Embodiment 3

One-Step Synthesis of Amoxicillin Catalyzed by Wild-Type and Penicillin Acylase Mutants Using PGK In PBS buffer at pH 7.0, PGK was added to reach a concentration of 200 mM, along with D-p-Hydroxyphenylglycine Methyl Ester (D-HPGM) to achieve a final concentration of 300 mM. Enzyme was added at 30 U/mL (based on synthetic activity). The reaction was carried out at 28° C. with constant stirring for 3 hours. After the reaction, HPLC analysis was performed to calculate the yield of Amoxicillin.

HPLC Conditions: Agilent ZORBAX SB-C18 4.6×250 mm column, column temperature 25° C. Injection volume 10 µL. Mobile phase A (0.02 M $NaH_2PO_4$—$Na_2HPO_4$ buffer at pH 4.7), mobile phase B (methanol). Start with 90% mobile phase A and 10% mobile phase B for 5 minutes, increase mobile phase B from 10% to 50% between 5 and 7 minutes, maintain 50% for 10 minutes, reduce mobile phase B from 50% to 10% between 17 and 19 minutes, and finally equilibrate with 90% mobile phase A and 10% mobile phase B for 5 minutes. Flow rate is 1 mL/min.

The reaction scheme is as follows:

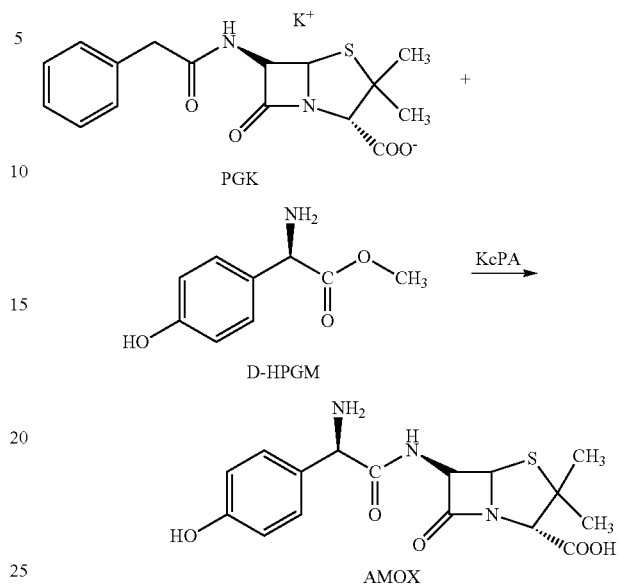

Figure 6:
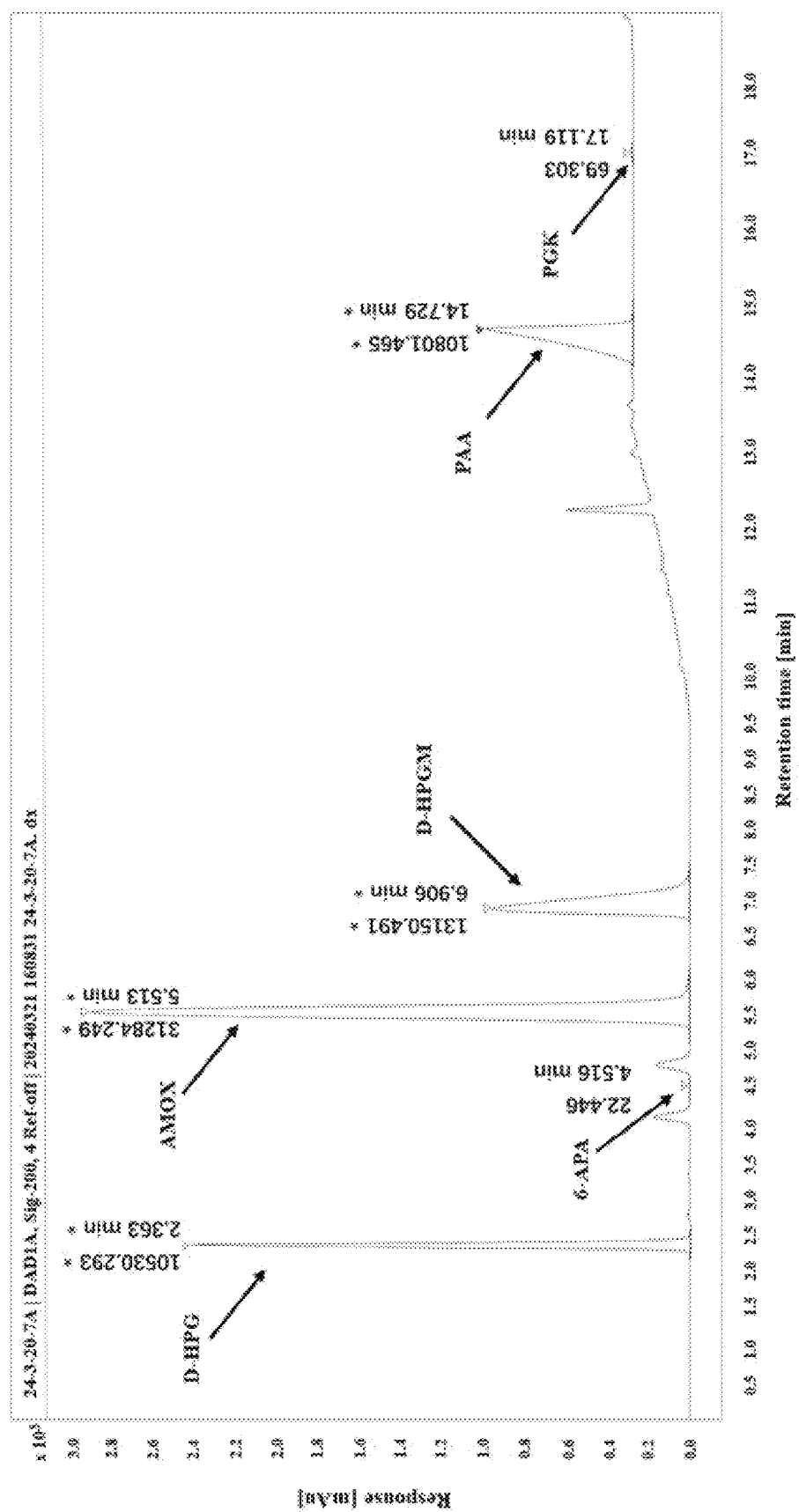
FIG. 6 illustrates the HPLC chromatogram of amoxicillin synthesized in a one-step reaction catalyzed by KcPA from penicillin potassium salt in Embodiment 3.

For mutant KcPA 18, the HPLC detection spectrum is shown in FIG. 6, where D-HPG represents D-p-Hydroxyphenylglycine, AMOX represents Amoxicillin, D-HPGM represents D-p-Hydroxyphenylglycine Methyl Ester, PAA represents Phenylacetic Acid, and PGK represents Penicillin Potassium Salt. As can be seen from the figure, the content of the intermediate 6-APA is extremely low, almost negligible.

TABLE 3

Yield of Amoxicillin Catalyzed by Various Mutants

| Mutant ID | Amoxicillin Yield/% |
|---|---|
| KcPA | 8.5 |
| KcPA 01 | 24.5 |
| KcPA 02 | 16.3 |
| KcPA 03 | 18.6 |
| KcPA 04 | 17.2 |
| KcPA 05 | 15.7 |
| KcPA 06 | 20.1 |
| KcPA 07 | 26.8 |
| KcPA 08 | 28.5 |
| KcPA 09 | 25.3 |
| KcPA 10 | 29.2 |
| KcPA 11 | 34.7 |
| KcPA 12 | 28.9 |
| KcPA 13 | 68.2 |
| KcPA 14 | 85.6 |
| KcPA 15 | 37.7 |
| KcPA 16 | 67.9 |
| KcPA 17 | 92.8 |
| KcPA 18 | 99.0 |

From the results in the table above, it is evident that all mutants are capable of catalyzing the reaction between potassium salt of penicillin and D-Hydroxyphenylglycine Methyl Ester in one step to synthesize Amoxicillin within a single reaction system. Moreover, the product yields are significantly higher compared to the wild type.

Embodiment 4

Preparation of Immobilized Penicillin Acylase

Penicillin acylase enzyme solution was prepared according to Embodiment 1. This enzyme solution was then added to epoxy resin (ER) activated with glutaraldehyde, and the cross-linking reaction was carried out at 15° C. for 1.5 hours. The cross-linking reaction system consisted of: 1200 U of enzyme solution, 0.25% glutaraldehyde, 5 g of ER, and 50 mL of phosphate buffer ($KH_2PO_4$—$K_2HPO_4$) at pH 7.5. After the completion of the cross-linking reaction, the immobilized enzyme was collected by filtration using a sieve. The immobilized enzyme was then washed with 100 mL of phosphate buffer (pH 7.5). The activity of the immobilized enzyme was measured to be 180 U/g, with an immobilized enzyme activity recovery rate reaching 75%.

Embodiment 5

One Step Synthesis of Amoxicillin from PGK Catalyzed by KcPA 18
  (1) In a reaction flask, 50 mL of PBS buffer at pH 7 was added as the reaction buffer system.
  (2) A certain amount of Penicillin Potassium Salt (PGK) and D-p-Hydroxyphenylglycine Methyl Ester (D-HPGM) was accurately weighed and introduced into the reaction buffer system. The molar ratio of PGK to D-HPGM was in the range of 1:1 to 1:2. The concentration of PGK was in the range of 50-200 mmol/L, and the concentration of D-HPGM was in the range of 50-400 mmol/L. The mixture was then thoroughly stirred to ensure uniform dispersion of the substrates PGK and D-HPGM in the reaction system. In this example, the final concentrations of PGK and D-HPGM were 200 mmol/L and 300 mmol/L, respectively.
  (3) The penicillin acylase mutant enzyme solution, KcPA18, was immobilized according to the method described in Embodiments 4. A known amount of the immobilized enzyme was accurately weighed and added to the reaction flask. The enzyme dosage was 20 U/mL (calculated based on synthetic activity). The reaction temperature was controlled at 24° C., and the reaction was carried out for 4 hours, yielding a milky-white reaction suspension.

Embodiment 6

Separation and Recovery of Amoxicillin and Phenylacetic Acid
1. Separation and Crystallization of Amoxicillin
  (1) To 50 mL of the reaction suspension obtained in Example 5, an equal volume of deionized water was added.
  (2) The immobilized penicillin acylase was separated by filtration, followed by washing with 50 mL of deionized water. The filtrate and washings were collected and combined to a total volume of 150 mL.
  (3) 15% hydrochloric acid was added dropwise to the filtrate until the pH reached approximately 2, yielding a mixture ready for separation.
  (4) 0.25 mol/L NaOH solution was then added dropwise to the mixture until the pH reached 5. The mixture was placed in a refrigerator at 4° C. for crystallization over 9 hours.
  (5) After crystallization, the mixture was filtered, yielding amoxicillin crystals and a liquid phase containing phenylacetic acid. The amoxicillin crystals were dried in an oven at 85° C. for 30 minutes.

Figure 7:
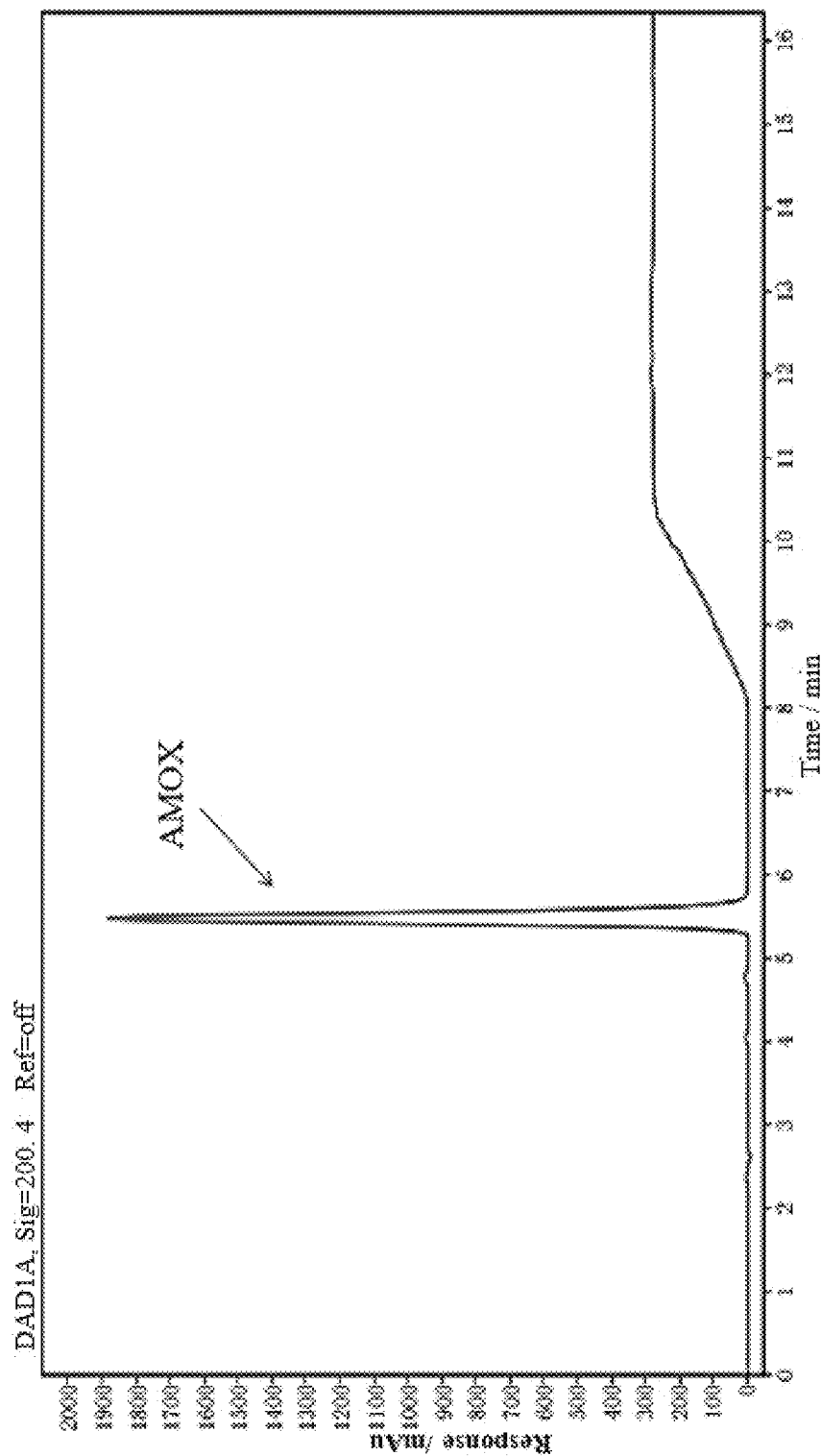
FIG. 7 is a liquid chromatography chart of the amoxicillin crystal product.

To verify if the crystallized product is indeed amoxicillin, 0.1 g of the crystalline product was dissolved in deionized water and diluted to 50 mL, resulting in a 2 mg/mL solution. High-performance liquid chromatography (HPLC) analysis was performed under conditions identical to those described in Example 3. As shown in FIG. 7, no significant impurity peaks other than the AMOX peak were observed, confirming that the crystal is primarily amoxicillin.

2. Separation and Crystallization of Phenylacetic Acid
  (1) The liquid phase containing phenylacetic acid (150 mL) was adjusted to a pH between 2.0 and 2.5 by adding 15% hydrochloric acid.
  (2) 40 mL of toluene was added as an extraction solvent. Extraction was performed at 25° C. with stirring for 15 minutes followed by settling to allow layer separation, transferring phenylacetic acid from the aqueous phase to the organic phase (toluene). This extraction process was repeated twice, and the organic phases were combined.
  (3) In the collected organic phase, 30 mL of 0.25 mol/L NaOH solution was added and thoroughly mixed. The mixture was allowed to settle (or centrifuged) to separate the layers, converting phenylacetic acid into sodium phenylacetate which was transferred back to the aqueous phase. The aqueous phase was separated from the organic phase, with the latter being recycled for further extractions in step (2).
  (4) The aqueous phase from the previous step (lower phase) was adjusted to a pH between 2.0 and 2.5 using 15% hydrochloric acid while heating at 60° C. It was then transferred to 4° C. for crystallization over 12 hours, converting sodium phenylacetate back into phenylacetic acid and allowing it to crystallize.
  (5) After crystallization, the mixture was filtered, and the residue was phenylacetic acid crystals. These crystals were dried in a vacuum oven at 40° C. for 30 minutes.

Figure 8:
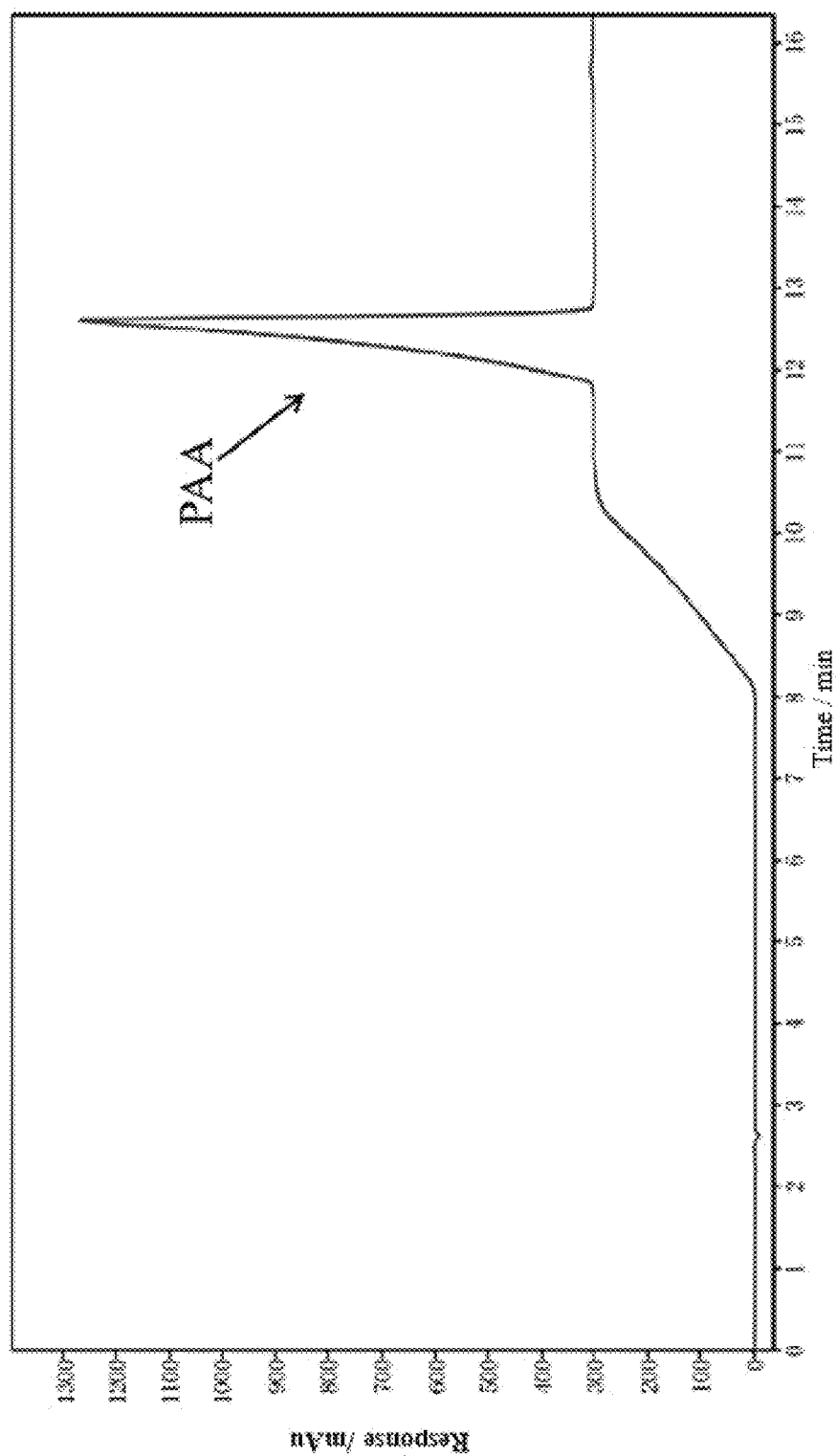
FIG. 8 is a liquid chromatography chart of the phenylacetic acid crystal product.

To verify if the crystallized product is indeed phenylacetic acid, 0.1 g of the crystalline product was dissolved in deionized water and diluted to 50 mL, resulting in a 2 mg/mL solution. HPLC analysis was performed under conditions identical to those described in Example 3. As shown in FIG. 8, no significant impurity peaks other than the PAA peak were observed, confirming that the crystal is primarily phenylacetic acid.

The above examples are merely preferred embodiments of the present invention and should not be construed as limiting the scope of the invention. Any modifications, substitutions, and improvements made within the spirit and principles of the invention are intended to be included within the scope of protection of the invention.

What is claimed is:

1. A method for separating amoxicillin and phenylacetic acid from a reaction solution obtained by a one-step enzymatic synthesis of amoxicillin, comprising catalyzing a one-step synthesis of amoxicillin from penicillin potassium using an immobilized penicillin acylase mutant to obtain a reaction suspension; and subjecting the reaction suspension to a separation process comprising the following steps:

(1) adding deionized water to the reaction suspension, and performing vacuum filtration to obtain an amoxicillin filtrate and a retained immobilized penicillin acylase mutant;

(2) washing the retained immobilized penicillin acylase mutant with deionized water, and combining a wash solution with the amoxicillin filtrate from step (1) to obtain a mixed solution;

(3) adjusting a pH of the mixed solution obtained in step (2) to 2 with hydrochloric acid to obtain a separation-ready mixture;

(4) adding a NaOH solution dropwise to the separation-ready mixture until reaching a pH between 3.5 and 5.5, followed by static crystallization at 4° C.; and (5) after the static crystallization is complete, filtering to obtain amoxicillin crystals and a liquid phase containing phenylacetic acid;

wherein a method for catalyzing the one-step synthesis of amoxicillin from the penicillin potassium using the immobilized penicillin acylase mutant comprises: using only one immobilized penicillin acylase mutant as a sole enzyme in a reaction system, with penicillin or a salt thereof and D-p-hydroxyphenylglycine methyl ester as substrates, and carrying out a reaction in a reaction buffer system of pH 4-8; wherein compared with the amino acid sequence shown in SEQ ID NO: 1, the immobilized penicillin acylase has mutations: F146αK and F24βR and F71βY and N241βY and G385βR.

2. The method according to claim 1, further comprising the following steps after step (5):

(6) adjusting a pH of the liquid phase containing phenylacetic acid to between 2.0 and 2.5, and extracting with toluene to obtain an organic phase containing phenylacetic acid;

(7) subjecting the organic phase containing phenylacetic acid to back-extraction with the NaOH solution, converting phenylacetic acid into sodium phenylacetate in an aqueous phase;

(8) separating the aqueous phase from the organic phase, wherein the organic phase is recycled for extraction in step (6);

(9) adding the hydrochloric acid to the aqueous phase containing sodium phenylacetate to adjust a pH to between 2.0 and 2.5, converting sodium phenylacetate into phenylacetic acid, followed by crystallization at 4° C.; and

(10) after the crystallization is complete, filtering to separate and recover phenylacetic acid crystals.

3. The method according to claim 1, wherein in step (3), a hydrochloric acid concentration is 15% by volume.

4. The method according to claim 1, wherein in step (4), the pH for the static crystallization is 5, and a crystallization time is 9 hours.

5. The method according to claim 1, wherein in step (5), after filtration and separation, the amoxicillin crystals are dried in a vacuum oven at 50° C. for 2 hours.

6. The method according to claim 2, wherein in step (6), the pH is adjusted using 15% by volume hydrochloric acid.

7. The method according to claim 2, wherein in step (6), extraction with toluene is performed at least twice, and resulting organic phases are combined.

* * * * *

SEQUENCE LISTING

```
Sequence total quantity: 16
SEQ ID NO: 1            moltype = AA  length = 846
FEATURE                 Location/Qualifiers
source                  1..846
                        mol_type = protein
                        organism = Kluyvera sp.
```

```
SEQUENCE: 1
MKNRNRMIVN GIVTSLICCS SLSALAASPP TEVKIVRDEY GMPHIYADDT YRLFYGYGYV     60
VAQDRLFQME MARRSTQGTV SEVLGKAFVS FDKDIRQNYW PDSIRAQIAS LSAEDKSILQ    120
GYADGMNAWI DKVNASPDKL LPQQFSTFGF KPKHWEPFDV AMIFVGTMAN RFSDSTSEID    180
NLALLTALKD KYGKQQGMAV FNQLKWLVNP SAPTTIAARE SAYPLKFDLQ NTQTAALLPR    240
YDQPAPMLDR PAKGTDGALL ALTADQNRET IAAQFAQSGA NGLAGYPTTS NMWVIGKNKA    300
QDAKAIMVNG PQFGWYAPAY TYGIGLHGAG YDVTGNTPFA YPGLVFGHNG TISWGSTAGF    360
GDDVDIFAEK LSAEKPGYYQ HNGEWVKMLS RKETIAVKDG QPETFTVWRT LHGNVIKTDT    420
ATQTAYAKAR AWDGKEVASL LAWTHQMKAK NWPEWTQQAA KQALTINWYY ADVNGNIGYV    480
HTGAYPDRQP GHDPRLPVPG TGKWDWKGLL SFDLNPKVYN PQSGYIANWN NSPQKDYPAS    540
DLFAFLWGGA DRVTEIDTIL DKQPRFTADQ AWDVIRQTSR RDLNLRLFLP ALKDATANLA    600
ENDPRRQLVD KLASWDGENL VNDDGKTYQQ PGSAILNAWL TSMLKRTVVA AVPAPFGKWY    660
SASGYETTQD GPTGSLNISV GAKILYEALQ GDKSPIPQAV DLFGGKPQQE VILAALDDAW    720
QTLSKRYGND VTGWKTPAMA LTFRANNFFG VPQAAAKEAR HQAEYQNRGT ENDMIVFSPT    780
SGNRPVLAWD VVAPGQSGFI APDGKADKHY DDQLIMYESF GRKSLWLTPQ DVDEHKESQE    840
VLQVQR                                                              846

SEQ ID NO: 2          moltype = DNA  length = 2541
FEATURE               Location/Qualifiers
source                1..2541
                      mol_type = genomic DNA
                      organism = Kluyvera sp.
SEQUENCE: 2
atgaaaaata gaaatcgtat gatcgtgaac ggtattgtga cttccctgat ctgttgttct     60
agcctgtcag cgctggcggc aagcccgcca accgaggtta agatcgttcg cgatgaatac    120
ggcatgccgc atatttacgc cgatgatacc tatcgactgt tttacggcta tggctacgtg    180
gtggcgcagg atcgcctgtt ccagatgaaa atggcgcgcc gcagtactca ggggaccgtc    240
tccgaggtgc tgggcaaagc attcgtcagt tttgataaag atattcgcca gaactactgg    300
ccggattcta ttcgcgcgca gatagcttcc ctctccgctg aggataaatc cattctgcag    360
ggctatgccg atggcatgaa tgcgtggatc gataaagtga agccagtccc cgataagctg    420
ttaccccagc agttctccac cttttggttt aaacccaagc attgggaacc gtttgatgtg    480
gcgatgattt tgtcggcac catggcgaac cgtttctctg acagcaccag cgaaattgat    540
aacctgcgc tgctgacggc gctaaaagat aaatacggca gcagcaggg catggcggtc    600
tttaaccagc tgctaatggt ggttaatcct tccgcgccaa ccaccattgc ggcgcgggaa    660
agcgcctatc cgctgaagtt tgatctgcaa aacacgcaaa cggccggctg gctgccgcgc    720
tacgaccagc cggcaccgat gctcgaccgc ccggcaaaag ggaccgatgg cgcgctgctg    780
gcgctgaccg ccgatcagaa ccgggaaact atcgccgcgc agttcgcgca aagcggcgct    840
aacggcctgg ctggctaccc gaccactagc aatatgtggg tgattggcaa aaacaaagcc    900
caggatgcga aggccattat ggtcaatggg ccgcagtttg gttggtatgc gccgcgtac    960
acctacggta tcggcctgca cggcgcgggc tatgacgtca ccggcaatac gccgttttgc    1020
tatccggggcc tcgttttgg tcacaacggc accatttcat ggggatccac cgccggtttt    1080
ggtgatgatg tcgatatctt tgccgaaaaa cttctccgccg agaagccggg ctattaccag    1140
cataacggcg agtgggtgaa gatgttgagc gcaaggaga ctattgcggt caaagacggc    1200
cagccggaga cctttaccgt tggcgcacg ctgcacggca acgtcattaa accgatact    1260
gcgacgcaga ccgcctatgc caaagcgcgc gcctgggatg gcaaagaggt ggcgtccctg    1320
ctggcgtgga cgcaccagat gaaggccaaa actggccgg agtggacgca gcaggcgcc    1380
aaacaggcgc tgaccattaa ctggtactac gccgatgtga acggcaatat ggctatgtg    1440
cataccggcg cctatccgga tcgccagccc ggccacgacc cgcgtttgcc ggttccggc    1500
actggaaaat gggactggaa agggttgctg tcgtttgatt tgaatccgaa agtgtataac    1560
ccgcagtcgg gctatatcgc caactggaac aactcgccgc aaaagactac ccggcctcc    1620
gatctgttcg cgttcctgtg gggcggtgcg gatcgagtta ctgagatcga cacgatcctc    1680
gataagcaac cgcgcttcac cgccgatcag cgtgggatg tgatccgcca aaccagccgt    1740
cgggatctca acctgcggtt gttcttaccg gcgctgaagg acgccaccgc gaacctggcg    1800
gaaaacgatc cgcgccgcca actggtggat aaactggcga gctgggacgg tgaaaacctt    1860
gtcaacgatg acggaaaaac ctatcagcaa ccgggatcgg cgattcttaa cgcctggctg    1920
accagcatgc tcaagcgcac ggtggttgcc gcggtcccag cgccgtttgg caagtggtac    1980
agcgccagtg gctatgaaac cacccaggac gggccaaccg gctcgctgaa catcagcgtg    2040
ggggcgaaaa tcctctacga agctctgcag ggtgataagt cgccaatccc gcaggcggtc    2100
gatctgtttg gcgggaaacc ggcagcggaa gtgatactgg cggcgctgga cgacgcttgg    2160
cagacgctgt caaaacgcta cggtaacgac gtcaccggct ggaaaacccc tgccatgcgg    2220
cttaccttcc gggccaataa cttcttcggc gtgccgcagg cggcagcaaa agaggcgcgt    2280
catcaggcgg agtaccagaa ccgcggtacg gaaaacgaca tgattgtctt ctcaccgacg    2340
tcgggtaacc gcccggttct tgcctgggat gtggtggcgc cggggcaaag cggtttatc    2400
gcgccggatg gcaaagccga taagcactat gacgatcagc tgataatgta cgagagcttt    2460
ggccgtaaat cgctcgtgtt aacgcctcag gacgttacg agcacaaaga gtctcaggaa    2520
gtgctgcagg tacagcgcta a                                             2541

SEQ ID NO: 3          moltype = DNA  length = 28
FEATURE               Location/Qualifiers
source                1..28
                      mol_type = other DNA
                      organism = synthetic construct
SEQUENCE: 3
cggaattcat gaaaaaccgc aatcgcat                                       28

SEQ ID NO: 4          moltype = DNA  length = 27
FEATURE               Location/Qualifiers
source                1..27
                      mol_type = other DNA
```

```
                                    organism = synthetic construct
SEQUENCE: 4
ccaagctttt agcgctgcac ctgcagc                                              27

SEQ ID NO: 5           moltype = DNA  length = 27
FEATURE                Location/Qualifiers
source                 1..27
                       mol_type = other DNA
                       organism = synthetic construct
SEQUENCE: 5
ggcgaaccgt aaatctgaca gcaccag                                              27

SEQ ID NO: 6           moltype = DNA  length = 25
FEATURE                Location/Qualifiers
source                 1..25
                       mol_type = other DNA
                       organism = synthetic construct
SEQUENCE: 6
atggtgccga caaaaatcat cgcca                                                25

SEQ ID NO: 7           moltype = DNA  length = 25
FEATURE                Location/Qualifiers
source                 1..25
                       mol_type = other DNA
                       organism = synthetic construct
SEQUENCE: 7
tgggccgcag cgcggttggt atgcg                                                25

SEQ ID NO: 8           moltype = DNA  length = 25
FEATURE                Location/Qualifiers
source                 1..25
                       mol_type = other DNA
                       organism = synthetic construct
SEQUENCE: 8
ttgaccataa tggccttcgc atcct                                                25

SEQ ID NO: 9           moltype = DNA  length = 23
FEATURE                Location/Qualifiers
source                 1..23
                       mol_type = other DNA
                       organism = synthetic construct
SEQUENCE: 9
caccgccggt tatggtgatg atg                                                  23

SEQ ID NO: 10          moltype = DNA  length = 25
FEATURE                Location/Qualifiers
source                 1..25
                       mol_type = other DNA
                       organism = synthetic construct
SEQUENCE: 10
gatcccatg aaatggtgcc gttgt                                                 25

SEQ ID NO: 11          moltype = DNA  length = 23
FEATURE                Location/Qualifiers
source                 1..23
                       mol_type = other DNA
                       organism = synthetic construct
SEQUENCE: 11
cgccaactgg aaaaactcgc cgc                                                  23

SEQ ID NO: 12          moltype = DNA  length = 26
FEATURE                Location/Qualifiers
source                 1..26
                       mol_type = other DNA
                       organism = synthetic construct
SEQUENCE: 12
atatagcccg actgcgggtt atacac                                               26

SEQ ID NO: 13          moltype = DNA  length = 31
FEATURE                Location/Qualifiers
source                 1..31
                       mol_type = other DNA
                       organism = synthetic construct
SEQUENCE: 13
cgggccaacc tattcgctga acatcagcgt g                                         31

SEQ ID NO: 14          moltype = DNA  length = 25
FEATURE                Location/Qualifiers
source                 1..25
```

```
                   mol_type = other DNA
                   organism = synthetic construct
SEQUENCE: 14
tcctgggtgg tttcatagcc actgg                                    25

SEQ ID NO: 15      moltype = DNA  length = 25
FEATURE            Location/Qualifiers
source             1..25
                   mol_type = other DNA
                   organism = synthetic construct
SEQUENCE: 15
cgggccaacc cgctcgctga acatc                                    25

SEQ ID NO: 16      moltype = DNA  length = 25
FEATURE            Location/Qualifiers
source             1..25
                   mol_type = other DNA
                   organism = synthetic construct
SEQUENCE: 16
tcctgggtgg tttcatagcc actgg                                    25
```